United States Patent
Severs

Patent Number: 5,814,025
Date of Patent: *Sep. 29, 1998

[54] SELF-VENTING FLUID SYSTEM

[75] Inventor: Dale Severs, Gurnee, Ill.

[73] Assignee: Baxter International Inc., Deerfield, Ill.

[*] Notice: The term of this patent shall not extend beyond the expiration date of Pat. No. 5,562,638.

[21] Appl. No.: 662,427

[22] Filed: Jun. 10, 1996

Related U.S. Application Data

[63] Continuation of Ser. No. 390,149, Feb. 16, 1995, Pat. No. 5,562,638, which is a continuation of Ser. No. 80,852, Jun. 21, 1993, abandoned.

[51] Int. Cl.$^6$ ................................................. A61M 5/32
[52] U.S. Cl. .................... 604/266; 604/80; 604/122; 604/265
[58] Field of Search ........................... 604/264–266, 604/280, 283, 122, 126, 80; 128/898

[56] References Cited

U.S. PATENT DOCUMENTS

| | | | |
|---|---|---|---|
| 3,831,813 | 8/1974 | Latham, Jr. | 604/80 |
| 4,324,239 | 4/1982 | Gordon et al. | 604/122 |
| 4,428,743 | 1/1984 | Heck | 604/122 |
| 4,535,819 | 8/1985 | Atkinson | 604/122 |
| 4,536,179 | 8/1985 | Anderson et al. | 604/266 |
| 4,686,124 | 8/1987 | Onohara | 604/266 |
| 4,784,644 | 11/1988 | Sawyer | 604/122 |
| 4,861,617 | 8/1989 | Pall | 604/266 |
| 4,976,685 | 12/1990 | Block, Jr. | 604/122 |
| 5,013,306 | 5/1991 | Solomon et al. | 604/265 |
| 5,019,601 | 5/1991 | Allen | 604/265 |
| 5,242,392 | 9/1993 | Vaughn | 604/80 |
| 5,342,621 | 8/1994 | Eury | 604/265 |
| 5,562,638 | 10/1996 | Severs | 604/266 |

OTHER PUBLICATIONS

Halliday & Resnick, Fundamentals of Physics, 2nd edition, pp. 207–208, 1970.
Fowles, Analytical Mechanics, 4th edition, pp. 45–46, 1980.
Fox & McDonald, Introduction to Fluid Mechanics, 3rd edition, pp. 682–685, 1985.

Primary Examiner—Michael Powell Buiz
Assistant Examiner—Chalin Smith
Attorney, Agent, or Firm—Thomas S. Borecki; Charles R. Mattenson; Robert M. Barrett

[57] ABSTRACT

A system and method is provided which substantially eliminates the effect of air entrapped in tubing for delivering a liquid from a container. The inner diameter of the tubing is selected such that the gravitational force of the liquid from the container is greater than the surface tension of the liquid. A release agent may be used as a coating layer on the interior wall in addition to or alternatively from an expanded diameter.

11 Claims, 1 Drawing Sheet

SELF-VENTING FLUID SYSTEM

This is a continuation, of application Ser. No. 08/390,149, filed on Feb. 16, 1995, now U.S. Pat. No. 5,562,638, which is a continuation of application U.S. Ser. No. 08/080,952, filed Jun. 21, 1993 now abandoned.

BACKGROUND OF THE INVENTION

The present invention generally relates to fluid delivery systems and more particularly to gravity fed fluid delivery systems.

Of course, it is known to provide containers for storing liquids. In, for example, the medical industry, it is known to provide flexible containers for containing solutions, such as, for example, medicaments, feeding products or the like. Such containers house solutions that can be delivered to a patient requiring an enteral solution, peritoneal dialysis, intravenous solutions, or the like.

Solutions contained within an interior of a flexible container are typically provided to a patient, or some other site, through a length of tubing connected to a port of the container. The tube provides fluid communication between the interior of the container and the patient or some other environment. The solution is typically gravity fed, but may be pumped or otherwise fed, to the patient from the container. To this end, the container is usually suspended.

Prior to initiation of the feeding of the solution, a portion of the solution must be drained from the tubing to expel air, generally in the form of air pockets or bubbles, in the system. Draining of the solution from the container results in a partial waste of the solution which is otherwise to be delivered to the patient.

A further issue that arises, especially when products are fed through a tube by gravity, is that air can be entrapped generally in the form of air bubbles, and escape from the tubing inversely to the direction of the solution flowing through the tubing. The air bubbles in the tubing undesirably result in an uneven flow of solution from the bag to the patient. Further, excessive entrapped air in the line may often terminate flow of solution to the patient for a dangerous period of time during delivery. Indeed, air entrapment can prevent any fluid flow through the tube.

To counteract fluid flow problems, it is known to vent the containers or tubing. However, this typically results in an open system that can compromise the sterility of the procedure.

A need, therefore, exists for an improved fluid delivery system eliminating the problem of air entrapment.

SUMMARY OF THE INVENTION

A fluid delivery system is provided having a fluid delivery tubing in fluid communication with an interior of a container. The tubing effectively provides a self-venting system eliminating air entrapment therein, allowing continuous flow of the solution from the container to the patient.

To this end, the present invention provides a delivery system for feeding a liquid from a container to a second site, for example, a patient. The system comprises a container and tubing in fluid communication with an interior of the container for receiving the liquid from the interior of the container. The tubing is so constructed and arranged so as to prevent air entrapment in the tubing during the transferring of the liquid from the interior to a second environment, e.g. patient.

In an embodiment, the tubing has an inner circumference that is sufficiently great so that the gravitational force on the liquid is greater than the surface tension of the liquid.

In an embodiment, the tubing has an inner circumferential wall coated with a release agent.

In an embodiment, the tubing has an inner circumferential wall including a release agent that is integrally formed therein.

In an embodiment, the release agent includes silicone.

In an embodiment, the present invention provides a delivery system for feeding, by gravity, a liquid to a patient. The system comprises a container having an interior. A tubing in fluid communication with the interior transfers the liquid from the interior to a patient. The tubing has an inner circumferential wall having a diameter that is sufficiently large so that the gravitational force on the fluid is greater than the surface tension of the fluid.

In an embodiment, the surface tension is reduced by coating the wall with a release agent.

In an embodiment, the surface tension is reduced by integrally forming in the wall a release agent.

In an embodiment, the present invention provides a method for delivering a liquid from an interior of a container. The method comprises the steps of suspending the container such that the liquid is fed by gravitational force, providing tubing for transferring of the liquid wherein tubing is constructed and arranged to eliminate air entrapment within the tubing, and feeding the liquid through the tubing.

In an embodiment, the tubing has an inner circumferential wall manufactured such that the gravitational force on the liquid is greater than the surface tension of the liquid.

It is, therefore, an advantage of the present invention to provide an improved system for transferring a liquid from a container to a second site.

Another advantage of the present invention is to provide an improved system for gravity feeding of a liquid from a container to a patient.

A further advantage of the present invention is to provide a system for eliminating air entrapment in a tubing for delivering a liquid from a container to a patient.

A still further advantage of the present invention is to provide a system for eliminating waste of liquid from the container in order to initiate delivery to a patient.

Moreover, an advantage of the present invention is to provide a system for providing a simple manner for eliminating entrapped air in a tubing for delivering a liquid.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a system and method for eliminating issues of air entrapment from closed fluid delivery systems. Although in the preferred embodiment set forth herein, the system is used for feeding of a solution from a container to a patient, it should be understood that the system and method of the present invention can be used for a variety of fluid transfer systems and in a variety of industries.

In the embodiment set forth herein, the system comprises a tubing connected to a port of a container providing fluid communication with an interior of the container. The tubing extends to the patient for feeding of a liquid, a solution or other fluid from the container.

Figure 1:
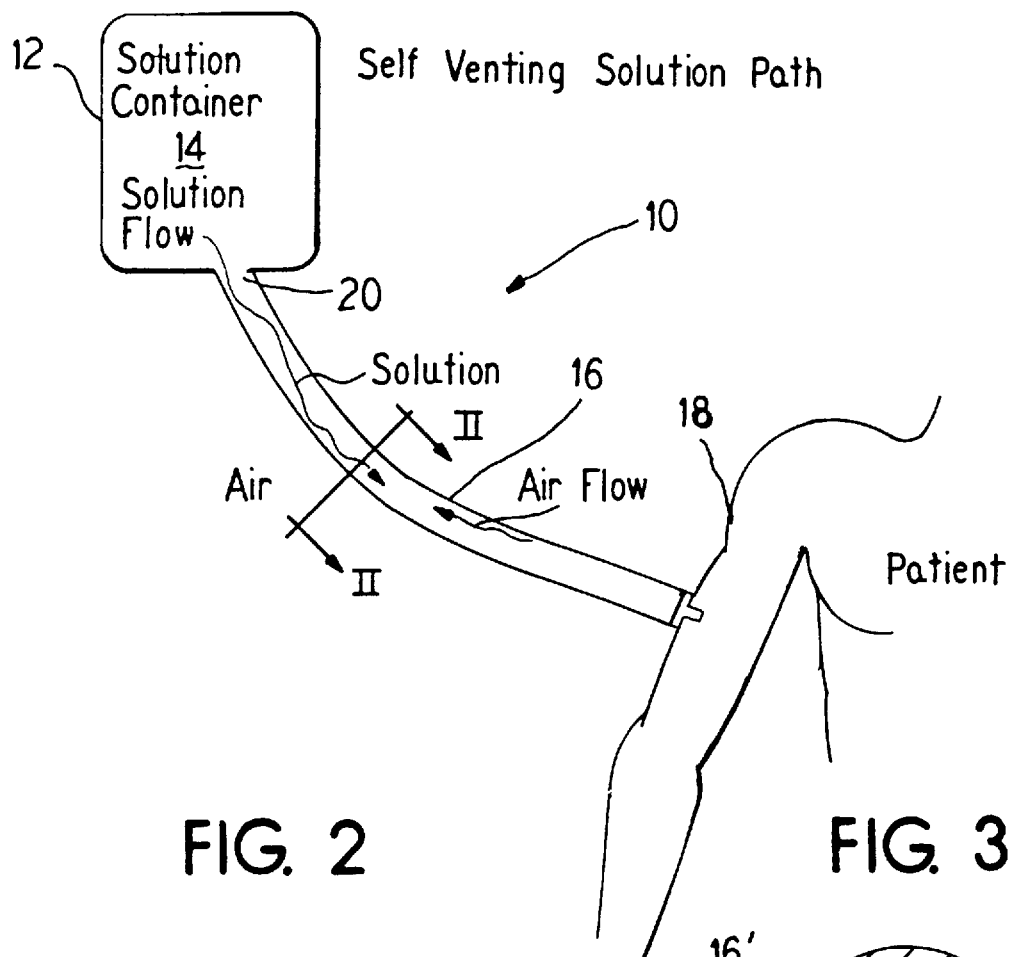
FIG. 1 illustrates a perspective view of a solution delivery system of the present invention.

Referring now to the drawings, FIG. 1 generally illustrates a system 10 having a container 12 for holding a liquid 14. The container 12 may be, for example, a sealed bag containing a peritoneal dialysis solution, an enteral feeding product, an intravenous solution, or the like for providing a medicament to a patient 18.

The container 12 includes a length of tubing 16 connected to a port 20 of the container 12. The container 12 is positioned at an elevation higher than an entry point of the tubing 16 to the patient 18. The port 20 provides fluid communication between an interior of the container 12 for the liquid 14 to flow from the container 12 through the tubing 16 to the patient 18.

As illustrated in FIG. 1, the tubing 16 is shown feeding an arm of the patient 18. Of course, the tubing 16 may be fed to any desired environment, for example a point of the body for the particular application, such as to the abdomen of the patient for peritoneal dialysis. Likewise, the tubing 16 can be fed to another container, to a pump, or a number of other locations.

Further, the port 20 may further include a connector (not shown) providing a means for connecting the tubing 16 to the container 12 at the port 20. The opposite end of the tubing 16, at the patient 18, is generally connected to another connector (not shown) for further connection to, for example, a syringe, a cannula or other like injection-type devices. The syringe or cannula is injected into the body of the patient for administration of the liquid 14 from the container 12 through the tubing 16.

Figure 2:
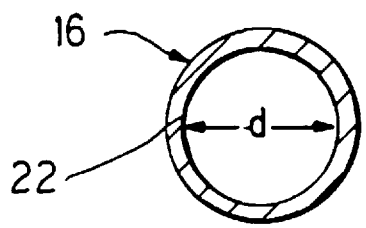
FIG. 2 illustrates a cross-sectional view of an embodiment of a tubing of the present invention taken generally along line II—II of FIG. 1.

In the embodiment of the system 10 illustrated in FIG. 1, the liquid 14 is gravity fed from the interior of the container 12 through the tubing 16. The tubing 16 has an inner circumferential wall 22 having a diameter d as illustrated in FIG. 2. Surface tension of the liquid 14 tends to prevent or to resist flow of the liquid 14 through the tubing 16.

In prior art systems, in particular closed systems, the surface tension of the liquid causes air to trap in the interior of the tubing since gravitational force on the liquid is less than the surface tension of the liquid. The air in the tubing of closed systems flows in a direction toward the container, that is, in a direction opposite the flow of the liquid. The air flow, therefore, creates air pockets or bubbles in the liquid in the interior of the tubing.

To overcome the problem of entrapped air, the tubing 16 of the present invention is manufactured such that the diameter d of the inner circumferential wall 22 allows a predetermined volume of liquid 14 to flow through the tubing 16 to counteract the surface tension of the liquid 14. The surface tension of the liquid 14 is, therefore, weaker than the gravitational force on the liquid 14 flowing through the tubing 16 from the container 12 to the patient 18. As a result, the diameter d allows a predetermined minimum volume of liquid 14 to flow evenly through the tubing 16 without entrapped air pockets.

To determine the appropriate diameter d for the tubing 16, the surface tension of the liquid merely needs to be identified. From this, the tubing 16 may be formed having a diameter d that causes the gravitational force on the liquid through the tubing 16 to be greater than the surface tension.

Figure 3:
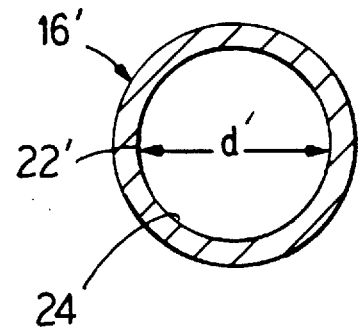
FIG. 3 illustrates a cross-sectional view of another embodiment of a tubing for use in the system of the present invention.

An alternative embodiment for the tubing 16 of FIG. 2 is illustrated in FIG. 3. A tubing 16' having an inner circumferential wall 22' having a diameter d' is shown. The inner wall 22' may have a coating layer 24 including a release agent, such as silicone, which effectively reduces the surface tension of the liquid. Of course, other release agents may be included in the coating layer 24 for reducing the surface tension of the liquid through the tubing 16'.

Alternatively, the release agent may be integrally formed in the inner wall 22' of the tubing 16'. The release agent, such as the silicone, reduces the surface tension of the liquid flowing through the tubing 16' with respect to the inner wall 22' which at least partially contacts the liquid flowing therethrough.

The release agent integrally forming at least a portion of the inner wall 22' of the tubing 16' or the coating layer 24 on the inner wall 22' reduces the diameter d' required in order for the gravitational force on the liquid to be greater than the surface tension of the liquid. Further, the release agent is selected such that the particular agent does not react with the liquid flowing through the tubing 16' from the container 12 to the patient 18.

It should, therefore, be understood that various changes and modifications to the presently preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

I claim as my invention:

1. A delivery system for allowing a selected liquid in an environment having constant temperature and constant pressure acting thereon to be fed from a container to a second environment in a closed system, the delivery system comprising:

a selected liquid having a density and an inherent surface tension at a constant temperature and at a constant pressure wherein the liquid is selected based upon calculations of gravitational force and surface tension;

a container having an interior holding the selected liquid; and a tubing suspended from the container and in fluid communication with the interior of the container wherein the tubing has a length and an angle of orientation with respect to a vertical axis wherein the length at the angle of orientation is defined between the container and the second environment and is so constructed and arranged to allow the selected liquid to flow from the interior of the container and through the tubing to counteract the inherent surface tension of the selected liquid in the tubing such that the inherent surface tension is less than a gravitational force on the selected liquid along the length of the tubing, thereby preventing air entrapment in the tubing wherein the tubing has an inner circumferential wall manufactured having a circumference selected such that the gravitational force on the selected liquid at all points along the length of the tubing is greater than the inherent surface tension of the selected liquid.

2. The system of claim 1 wherein the liquid is gravity fed from the container.

3. The system of claim 1 wherein the tubing has an inner circumferential wall coated with a release agent.

4. The system of claim 1 wherein the tubing has an inner circumferential wall including a release agent integrally formed therein.

5. The system of claim 3 wherein the release agent is silicone.

6. The system of claim 4 wherein the release agent is silicone.

7. A delivery system for feeding, by gravity, a selected liquid in an environment having constant temperature and a constant pressure acting thereon to a patient, the delivery system comprising:

a selected liquid having a density and an inherent surface tension at a constant temperature and at a constant pressure wherein the liquid is selected based upon calculations of gravitational force and surface tension;

a container having an interior holding the selected liquid; and a tubing suspended from the container and having a length and an angle of orientation with respect to a vertical axis wherein the length at the angle of orientation is defined between the container and the patient in fluid communication with the interior transferring the selected liquid from the interior of the container to the patient wherein the tubing has an inner circumferential wall manufactured such that gravitational force on the selected liquid along the length of the tubing is greater than the inherent surface tension of the selected liquid wherein the inner circumferential wall has a circumference selected such that the gravitational force on the liquid at all points along the length of the tubing is greater than the inherent surface tension.

8. The system of claim 7 wherein the surface tension is reduced by coating the wall with a release agent.

9. The system of claim 7 wherein the surface tension is reduced by integrally forming the wall with a release agent.

10. The system of claim 8 wherein the release agent is silicone.

11. A delivery system for allowing a selected liquid in an environment having constant temperature and a constant pressure acting thereon to be fed from a container to a second environment in a closed system, the delivery system comprising:

a selected liquid having a density and an inherent surface tension at a constant temperature and a constant pressure wherein the liquid is selected based upon calculations of gravitational force and surface tension;

a container having an interior holding the selected liquid; and a tubing suspended from the container and in fluid communication with the interior of the container wherein the tubing has a length and an angle of orientation with respect to a vertical axis wherein the length at the angle of orientation is defined between the container and the second environment and is so constructed and arranged to allow the selected liquid to flow from the interior of the container and through the tubing to counteract the inherent surface tension of the selected liquid in the tubing such that the inherent surface tension is less than a gravitational force on the selected liquid along the length of the tubing, thereby preventing air entrapment in the tubing, wherein the tubing has an inner circumferential wall including a release agent integrally formed therein and further wherein the release agent is silicone.

* * * * *